United States Patent [19]

Grollier et al.

[11] Patent Number: 4,513,011
[45] Date of Patent: Apr. 23, 1985

[54] COMPOSITION IN THE FORM OF A SHAMPOO BASED ON ANTHRALIN

[75] Inventors: Jean-François Grollier, Paris; Georges Rosenbaum, Asnieres; Josiane Allec, Pierrefitte; Braham Shroot, Antibes, all of France

[73] Assignee: L'Oreal, Paris, France

[21] Appl. No.: 436,046

[22] Filed: Oct. 22, 1982

[30] Foreign Application Priority Data

Oct. 23, 1981 [FR] France ................. 81 19952
Apr. 5, 1982 [FR] France ................. 82 05864

[51] Int. Cl.³ .............................................. A61K 31/05
[52] U.S. Cl. ................................... 514/730; 514/863; 514/970
[58] Field of Search ........................................ 424/346

[56] References Cited

U.S. PATENT DOCUMENTS 3,881,000 4/1975 Freidmann et al. ................ 424/209
4,367,224 1/1983 Van Scott et al. .................. 424/175

Primary Examiner—Leonard Schenkman
Attorney, Agent, or Firm—Wegner & Bretschneider

[57] ABSTRACT

Composition in the form of a shampoo based on anthralin or one of its derivatives.

This composition contains in aqueous solution or dispersion:

anthralin or one of its derivatives,
at least one fatty acid alkyl ester, the fatty acid having 5 to 8 carbon atoms and the alkyl radical having 3 to 18 carbon atoms,
at least one anionic or nonionic surfactant,
that composition being stable to oxidation for approximately one week when stored at a temperature of approximately +4° C.

This composition is used in the treatment of the scalp, particularly for psoriasis.

5 Claims, No Drawings

COMPOSITION IN THE FORM OF A SHAMPOO BASED ON ANTHRALIN

The present invention has as an object a composition in the form of a shampoo based on anthralin or one of its derivatives and its use in the treatment of diseases of the scalp, particularly psoriasis.

Psoriasis is a particularly common dermatosis producing lesions which are encountered not only on the elbows, the posterior surface of the forearm, the knees, the legs, and the sacrolumbar regions, but also on the scalp.

Among the various substances which have already been recommended for the treatment of psoriasis, one should very specifically mention anthralin or dithranol (1,8,9-trihydroxyanthracene), which has proven particularly active but is not without certain disadvantages, inasmuch as this compound is very readily degraded by oxidation to dark-colored polymeric products capable of staining the skin and clothing.

Furthermore, known compositions, which generally use a petroleum jelly base as a support, are not very suitable for treatment of the scalp, since they are difficult to remove.

Up to now, compositions in shampoo form have never been recommended, because of the very great instability of anthralin and its derivatives in aqueous solution. In effect, the compositions change color after only a few hours, denoting a decomposition of the anthralin. This decomposition is also a result of the presence of a surfactant, which can have a degrading effect.

After numerous studies in this field, it was possible to develop shampoos showing good stability to oxidation which can be stored without degradation for approximately one week at a temperature of approximately +4° C. This permits the same shampoo to be used for several treatments after mixture of the anhydrous part and the aqueous part of the compositions of this invention, which are packaged in two parts, without having to make up a new mixture at the moment of each use.

This good stability of the shampoos of this invention is essentially due to the presence of certain fatty acid alkyl esters and the presence of certain surfactants, specifically of the anionic or nonionic type.

The present invention has as an object a composition in the form of a shampoo based on anthralin or one of its derivatives for the treatment of the scalp. This solution contains the following in aqueous solution or dispersion: anthralin or one of its derivatives; a fatty acid alkyl ester from a $C_5$–$C_{18}$ fatty acid and a branched or unbranched 3-18 carbon alkyl radical; and at least one anionic or nonionic surfactant. This composition is stable with respect to oxidation for at least one week when stored at a temperature of approximately 4° C.

Fatty acid alkyl esters responding to the above definition include: isodecyl neopentanoate, cetyl octanoate, stearyl octanoate, isopropyl laurate, ethyl myristate, isopropyl myristate, isopropyl palmitate, 2-ethylhexyl palmitate, butyl stearate, isopropyl stearate, 2-ethylhexyl stearate, isocetyl stearate, and mixtures of these substances.

Anthralin derivatives which can be stabilized by fatty acid alkyl esters include the compounds described in French Patent Application Nos. 80,22454 and 80,22455.

The anionic or nonionic surfactants which can be used in the compositions of this invention are those producing solutions which show the same foaming capacity and a pH reduction of no more than 2 units after two months at 45° C.

Anionic surfactants which respond to this definition include:

$C_8$–$C_{18}$ alkylethersulfates such as sodium laurylethersulfate ethoxylated with 2.2 mols ethylene oxide;

$C_8$–$C_{18}$ acylsarcosines and their salts such as sodium cocoylsarcosinate.

$C_{10}$–$C_{20}$ α-olefinsulfonates such as sodium $C_{14}$–$C_{16}$ α-olefinsulfonates.

The anionic surfactants preferably used according to the invention which respond to the above definition are products of the condensation of monoalcohols, α-diols, alkylphenols, or alkanolamines with glycidol. The compounds particularly preferred are those responding to the following formulas:

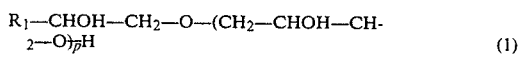
$$R_1-CHOH-CH_2-O-(CH_2-CHOH-CH_2-O)_pH \qquad (1)$$

where $R_1$ represents a $C_7$–$C_{21}$ aliphatic, cycloaliphatic, or arylaliphatic radical or a mixture of such radicals, where the aliphatic chains may carry ether, thioether, or hydroxymethane groups, and where p is between 1 and 10 inclusive. These compounds are more specifically described in French Pat. No. 2,091,516.

$$R_2O-[C_2H_3O(CH_2OH)]_qH \qquad (2)$$

where $R_2$ represents an alkyl, alkenyl, or alkylaryl radical and q is an average statistical value between 1 and 10 inclusive. These compounds are more specifically described in French Pat. No. 1,477,048; and

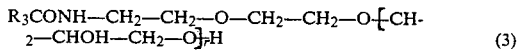
$$R_3CONH-CH_2-CH_2-O-CH_2-CH_2-O-[CH_2-CHOH-CH_2-O]_rH \qquad (3)$$

where $R_3$ represents a linear or branched, saturated or unsaturated $C_8$–$C_{30}$ aliphatic radical which may optionally carry one or more hydroxyl groups and which may be of natural or synthetic origin, or a mixture of such radicals, and where r represents a whole or decimal number between 1 and 5 and specifies the average degree of condensation. These compounds are more specifically described in French Pat. No. 2,328,763.

Nonionic surfactants which give particularly useful results in the compositions of this invention respond to the following formulas:

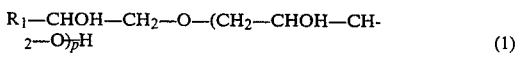
$$R_1-CHOH-CH_2-O-(CH_2-CHOH-CH_2-O)_pH \qquad (1)$$

in which $R_1$ represents a mixture of $C_9$–$C_{12}$ alkyl radicals and p has a statistical value of 3.5;

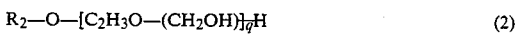
$$R_2-O-[C_2H_3O-(CH_2OH)]_qH \qquad (2)$$

in which $R_2$ represents $C_{12}H_{25}$ and q has a statistical value of 4 to 5; and

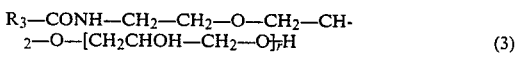
$$R_3-CONH-CH_2-CH_2-O-CH_2-CH_2-O-[CH_2CHOH-CH_2-O]_rH \qquad (3)$$

in which $R_3$ represents a mixture of radicals derived from lauric, myristic, oleic, and coprah acids and r has a statistical value of 3 to 4.

According to this invention, the concentration of anthralin or one of its derivatives in the composition is generally between 0.01 and 5%, but preferably between 0.03 and 2%. The concentration of fatty acid alkyl ester is between 8 and 47.5%, and that of the anionic or nonionic surfactant is between 2.5 and 36%. Percentages are by weight, referred to the total weight of the composition.

The shampoo composition may also contain various miscellaneous ingredients, as long as these ingredients have no undesirable effect on stability. In particular, such ingredients include certain thickening agents such as silicas and polyethylene powders, preferably present at a concentration between 0.1 and 20 wt%, particularly between 2 and 15 wt%.

The shampoo composition of this invention is generally prepared at the moment of its first use by mixing an anhydrous part and an aqueous part; thus it is preferably made available in the form of a two-part package.

The first or anhydrous part contains the anthralin or anthralin derivative dissolved or dispersed in the fatty acid alkyl ester, which is stable with respect to oxidation with no necessity for incorporating a stabilizer or antioxidant. The second or aqueous part contains a solution of the anionic or nonionic surfactant in water, generally at a pH between 3 and 7, but preferably at an acid pH between 3 and 5 obtained, if necessary, by the addition of an acid such as citric, lactic, or acetic acid.

The concentration of anthralin or anthralin derivative in the anhydrous part is preferably between 0.1 and 5%. The concentration of the fatty acid alkyl ester is between 80 and 95%. This part may also contain an additional thickening agent.

The concentration of anionic or nonionic surfactant in the aqueous phase is preferably between 5 and 40%, preferably between 7 and 25%. The aqueous phase may also contain a thickening agent.

At the moment of first use, the two parts are mixed in proportions which vary as a function of the effectiveness desired, generally in a ratio of the anhydrous part to the aqueous part between 10:90 and 50:50. The mixture obtained is then applied to the scalp and hair in an amount of approximately 20 to 30 g. The mixture is then allowed to act for approximately 5 min to 1 h, emulsified with water, and rinsed out with abundant quantities of water. This treatment is continued every day or every other day using the same composition, after storing it at approximately +4° C.

In general, the two-part package is such as to permit, after mixing, a one-week treatment at the rate of one or two shampoo treatments every two days.

The anhydrous part is preferably packaged in sealed glass ampoules. The aqueous part is preferably packaged in bottles. At the moment of use, the tip of the ampoule is broken and the solution or dispersion is poured into the bottle. It is recommended that the mixture be agitated thoroughly before each use.

Good results are generally obtained in the treatment of psoriasis after 3 to 5 weeks.

Several non-limiting examples of the compositions of this invention will now be given to illustrate it.

EXAMPLE 1

A shampoo according to this invention was packaged in the form of the following two parts:

| (1) Anhydrous part | |
|---|---|
| Anthralin | 0.83 g |
| 50:50 mixture of cetyl octanoate and stearyl octanoate to make | 100 g |
| (2) Aqueous part | |
| Sodium laurylethersulfate ethoxylated with 2.2 mols ethylene oxide | 12 g |
| Lactic acid to pH 4 | |
| Water to make | 100 g |

At the moment of use, 25% of the anhydrous part (1) and 75% of the aqueous part (2) were mixed.

The resulting composition had a milky appearance, and approximately 30 g were appied to the scalp and hair.

After 20 min, it was emulsified with water and rinsed off.

The remaining composition remained stable for approximately 7 days when stored at a temperature of approximately +4° C., permitting 2 to 3 shampoo treatments to be performed at intervals of one day.

After two weeks, a regression in the psoriasis was observed. The treatment can be continued, spacing the shampoo treatments a day or two apart.

In this example, the anhydrous part can be replaced with one of the following compositions:

| (a) Anthralin | 0.4 g |
|---|---|
| Isopropyl myristate to make | 100 g |
| (b) Anthralin | 0.47 g |
| Ethyl myristate to make | 100 g |
| (c) Anthralin | 0.20 g |
| Isocetyl stearate to make | 100 g |

EXAMPLES 2-6

Using the same operating method as in Example 1, psoriasis of the scalp was treated with shampoos obtained after mixing the following two-part compositions:

EXAMPLE 2

| (1) Anhydrous part | |
|---|---|
| Anthralin | 0.2 g |
| Isopropyl myristate to make | 100 g |
| (2) Aqueous part | |
| Nonionic surfactant of the formula: $R_1-CHOH-CH_2-O+CH_2-CHOH-CH_2-O\!\!\rightarrow_{\!p}\!\!-H$ $R_1 = C_9-C_{12}$ alkyl, $p = 3.5$ | 20 g |
| Formaldehyde | 0.06 g |
| Citric acid to pH 3 | |
| Water to make | 100 g |

At the moment of use, 25% anhydrous part (1) was mixed with 75% aqueous part (2).

EXAMPLE 3

| (1) Anhydrous part | |
|---|---|
| Anthralin | 0.4 g |
| Isopropyl palmitate to make | 100 g |
| (2) Aqueous part | |
| Nonionic surfactant of the formula: $R_1-CHOH-CH_2-O+CH_2-CHOH-CH_2-O\!\!\rightarrow_{\!p}\!\!-H$ $R_1 = C_9-C_{12}$ alkyl, $p = 3.5$ | 20 g |
| Formaldehyde | 0.06 g |
| Citric acid to pH 3 | |
| Water to make | 100 g |

At the moment of use, 25% anhydrous part (1) was mixed with 75% aqueous part (2).

EXAMPLE 4

| (1) Anhydrous part | |
|---|---|
| Anthralin | 0.47 g |
| Ethyl myristate to make | 100 g |
| (2) Aqueous part | |
| Cocoylsarcosinic acid (Sold by Societe Hampschire under the name "Hamposyl-C" | 17 g |
| | (active substance) |
| Sodium hydroxide to pH 4.5 | |
| EDTA | 0.07 g |
| Water to make | 100 g |

At the moment of use, 15% anhydrous part (1) was mixed with 85% aqueous part (2).

In this example, the anhydrous part (1) can be replaced with one of the following compositions:

| (a) Anthralin | 0.40 g |
|---|---|
| Isopropyl myristate to make | 100 g |
| (b) Anthralin | 0.20 g |
| Isocetyl stearate | 100 g |

EXAMPLE 5

| (1) Anhydrous part | |
|---|---|
| Anthralin | 0.2 g |
| Isocetyl stearate to make | 100 g |
| (2) Aqueous part | |
| Sodium α-olefin ($C_{14}$-$C_{16}$) sulfonate (sold by Societe Akzo Chemie under the name "Elfan OS 46" | 16.5 g |
| | (active substance) |
| Citric acid to pH 3.5 | |
| Water to make | 100 g |

At the moment of use, 20% anhydrous part (1) was mixed with 80% aqueous part (2).

In this example, the anhydrous part (1) can be replaced with one of the following compositions:

| (a) Anthralin | 0.4 g |
|---|---|
| Isopropyl myristate to make | 100 g |
| (b) Anthralin | 0.83 g |
| 50:50 mixture of cetyl octoanate and stearyl octoanate to make | 100 g |
| (c) Anthralin | 0.47 g |
| Ethyl myristate to make | 100 g |

EXAMPLE 6

| (1) Anhydrous part | |
|---|---|
| Anthralin | 0.47 g |
| Ethyl myristate to make | 100 g |
| (2) Aqueous part | |
| Nonionic surfactant of the formula: $R_1$—CHOH—$CH_2$—O—($CH_2$—CHOH—$CH_2$—O)$_p$—H $R_1$ = $C_9$-$C_{12}$ alkyl, p = 3.5 | 20 g |
| Acetic acid to pH 5 | |
| Thickening agent | 2.3 g |
| Water to make | 100 g |

At the moment of use 25% anhydrous part (1) was mixed with 75% aqueous part (2).

In this example, the anhydrous part (1) can be replaced with one of the following compositions:

| (a) Anthralin | 2 g |
|---|---|
| 50:50 mixture of cetyl octanoate and ethyl octanoate to make | 100 g |
| (b) Anthralin | 1.5 g |
| Isocetyl stearate to make | 100 g |

All the shampoos of Examples 2 to 6 showed good stability during storage at a temperature of approximately +4° C. for one week, as well as excellent activity in the treatment of psoriasis of the scalp.

We claim:

1. A shampoo composition for the treatment of the scalp which contains in aqueous solution or dispersion 0.01 to 5 percent by weight of anthralin, 8 to 47.5 percent by weight of an acid alkyl ester selected from the group consisting of ethyl myristate and acid alkyl esters in which the fatty acid has 5 to 18 carbon atoms and the alkyl radical has 3 to 18 carbon atoms, and 2.5 to 36 percent by weight of an anionic or nonionic surfactant, the composition being stable to oxidation for approximately one week when stored at a temperature of approximately +4° C.

2. The shampoo composition of claim 1 in which the fatty acid alkyl ester is selected from the group consisting of: isodecyl neopentanoate, cetyl octanoate, stearyl octanoate, isopropyl laurate, isopropyl myristate, isopropyl palmitate, 2-ethylhexyl stearate, isocetyl stearate and mixtures thereof.

3. The shampoo composition of claim 1, wherein the anionic surfactant is selected from the group consisting of: $C_8$-$C_{18}$ alkyl ethersulfates, $C_8$-$C_{18}$ acylsarcosines and their salts, and $C_{10}$-$C_{20}$ α-olefin sulfonates.

4. The shampoo composition of claim 1 wherein the nonionic surfactant is selected from the group consisting of compounds of the formulas:

$$R_1\text{—CHOH—}CH_2\text{—O—}(CH_2\text{—CHOH—}CH_2\text{—O})_pH \quad (1)$$

in which $R_1$ represents a $C_7$-$C_{21}$ aliphatic, cycloaliphatic, or arylaliphatic radical or a mixture of such radicals in which the aliphatic chains may carry ether, thioether, or hydroxymethylene groups and where p is between 1 and 10, inclusive;

$$R_2O\text{—}[C_2H_3O(CH_2OH)]_q\text{H} \quad (2)$$

in which $R_2$ represents an alkyl, alkenyl, or alkylaryl radical and q is an average statistical value between 1 and 10, inclusive, and $$R_3CONH\text{—}CH_2\text{—}CH_2\text{—O—}CH_2\text{—}CH_2\text{—O}[CH_2\text{—CHOH—}CH_2]_r\text{H} \quad (3)$$

in which $R_3$ represents a $C_8$-$C_{30}$ aliphatic radical or mixture of such radicals, of natural or synthetic origin, which may be linear or branched, saturated or unsaturated, and may optionally carry one or more hydroxyl groups, and in which r is a whole or decimal number from 1 to 5 representing the average degree of condensation.

5. The shampoo composition of claim 1, which also contains a thickening agent at a concentration between 0.1 and 20 percent by weight.

* * * * *